US00PP31430P3

(12) United States Plant Patent
van Langen

(10) Patent No.: US PP31,430 P3
(45) Date of Patent: Feb. 4, 2020

(54) ***ALOE* X *HAWORTHIA* HYBRID PLANT NAMED 'AMIAL 1601'**

(50) Latin Name: ***Aloe aristata* x *Haworthia limifolia***
Varietal Denomination: AMIAL 1601

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/932,615

(22) Filed: Mar. 23, 2018

(65) Prior Publication Data

US 2019/0297767 P1 Sep. 26, 2019

(51) Int. Cl.
*A01H 5/12* (2018.01)
*A01H 6/00* (2018.01)

(52) U.S. Cl.
USPC ..... Plt./373

CPC ..... *A01H 6/00* (2018.05); *A01H 5/12* (2013.01)

(58) Field of Classification Search
USPC ..... Plt./373
See application file for complete search history.

(56) References Cited

PUBLICATIONS

UPOV hit on *Aloe x Haworthia* hybrid plant name, 'Amial1601', QZ PBR 49415, published Dec. 16, 2016.*

* cited by examiner

*Primary Examiner* — Anne Marie Grunberg
(74) *Attorney, Agent, or Firm* — Samuel R. McCoy, Jr.

(57) ABSTRACT

A new and distinct *Aloe aristata* x *Haworthia limifolia* hybrid plant named 'AMIAL1601', which is characterized by long, broad and thick succulent foliage, foliage arranged in multiple whorls which, together, create a tall rosette, and dark green foliage with very light green orbicular protuberances arranged in irregular, wavy transverse rows across the upper and lower leaf surfaces. The new variety has shown to be uniform and stable in the resulting generations from asexual propagation.

4 Drawing Sheets

Latin name of the genus and species: The Latin name of the genus and species of the novel variety disclosed herein is *Aloe aristata* x *Haworthia limifolia.*

Variety denomination: The inventive variety of *Aloe* x *Haworthia* hybrid disclosed herein has been given the variety denomination 'AMIAL1601'.

BACKGROUND OF THE INVENTION

Parentage: 'AMIAL1601' is an intergeneric hybrid seedling selection resulting from the controlled pollination of an unnamed *Aloe aristata* plant (not patented), the seed parent, with an unnamed *Haworthia limifolia* plant (not patented), the pollen parent. The crossing was made by the inventor in the spring of 2011 at a commercial greenhouse in Heerhugowaard, the Netherlands. In the summer of 2013, one seedling was observed which exhibited unique growth and foliage characteristics. After confirming the stability of the unique characteristics first observed, the new plant was selected for commercialization and given the name, 'AMIAL1601'.

Asexual Reproduction: Asexual reproduction of the new cultivar 'AMIAL1601', by way of rooting leaf cuttings, was first initiated in the summer of 2014 at the inventor's commercial greenhouse in Heerhugowaard, the Netherlands. The claimed plant has since been asexually propagated by way of meristematic tissue culture propagation. Through five subsequent generations, the unique features of this cultivar have proven to be stable and true to type.

SUMMARY OF THE INVENTION

The cultivar 'AMIAL1601' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1601'. These characteristics in combination distinguish 'AMIAL1601' as a new and distinct *Aloe* x *Haworthia* hybrid cultivar:

1. 'AMIAL1601' exhibits succulent foliage arranged in multiple whorls which, together, create a tall rosette; and
2. 'AMIAL1601' exhibits inner whorls of foliage held upright and outer whorls of foliage held more loosely; and
3. 'AMIAL1601' exhibits long, broad and thick foliage with an ovate shape; and
4. 'AMIAL1601' exhibits dark green foliage with very light green orbicular protuberances arranged in irregular, wavy transverse rows across the upper and lower leaf surfaces.

BOTANICAL DESCRIPTION OF THE PLANT

Figure 1:
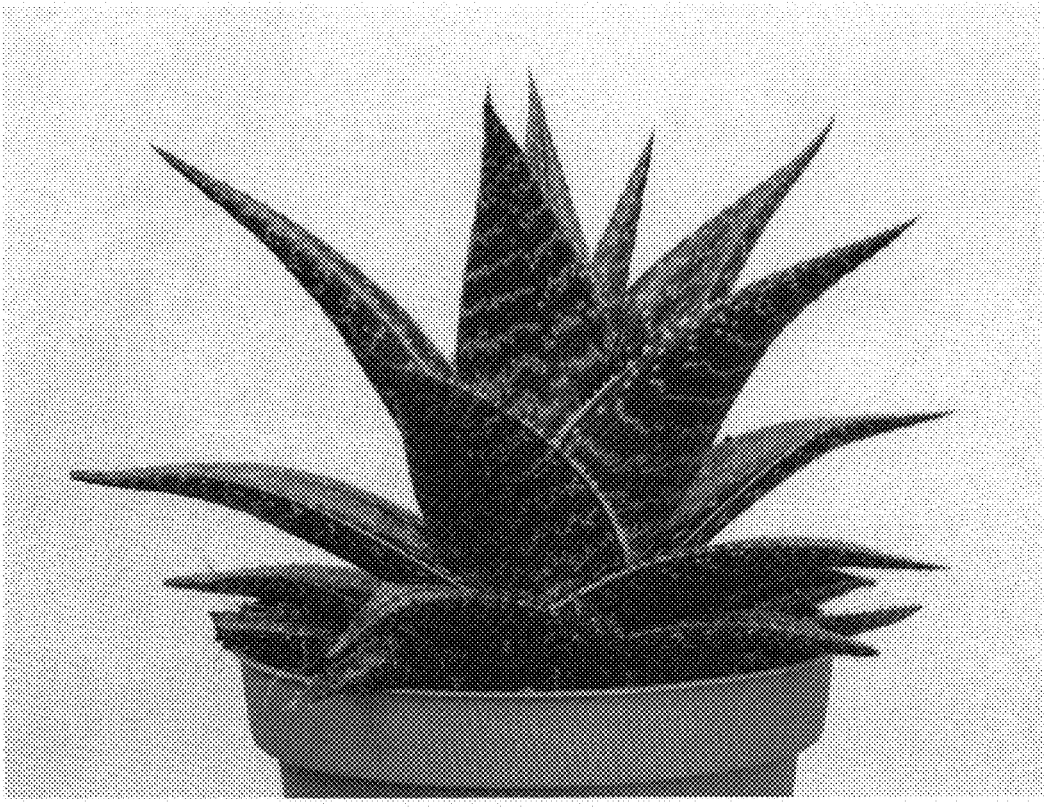
FIG. 1 illustrates, as nearly true as it is reasonably possible to make the same in color photographs of this type, an exemplary plant of 'AMIAL1601' grown in a commercial greenhouse in Heerhugowaard, the Netherlands. This plant is approximately 14 months old, shown planted in a 10 cm container.
Figure 2:
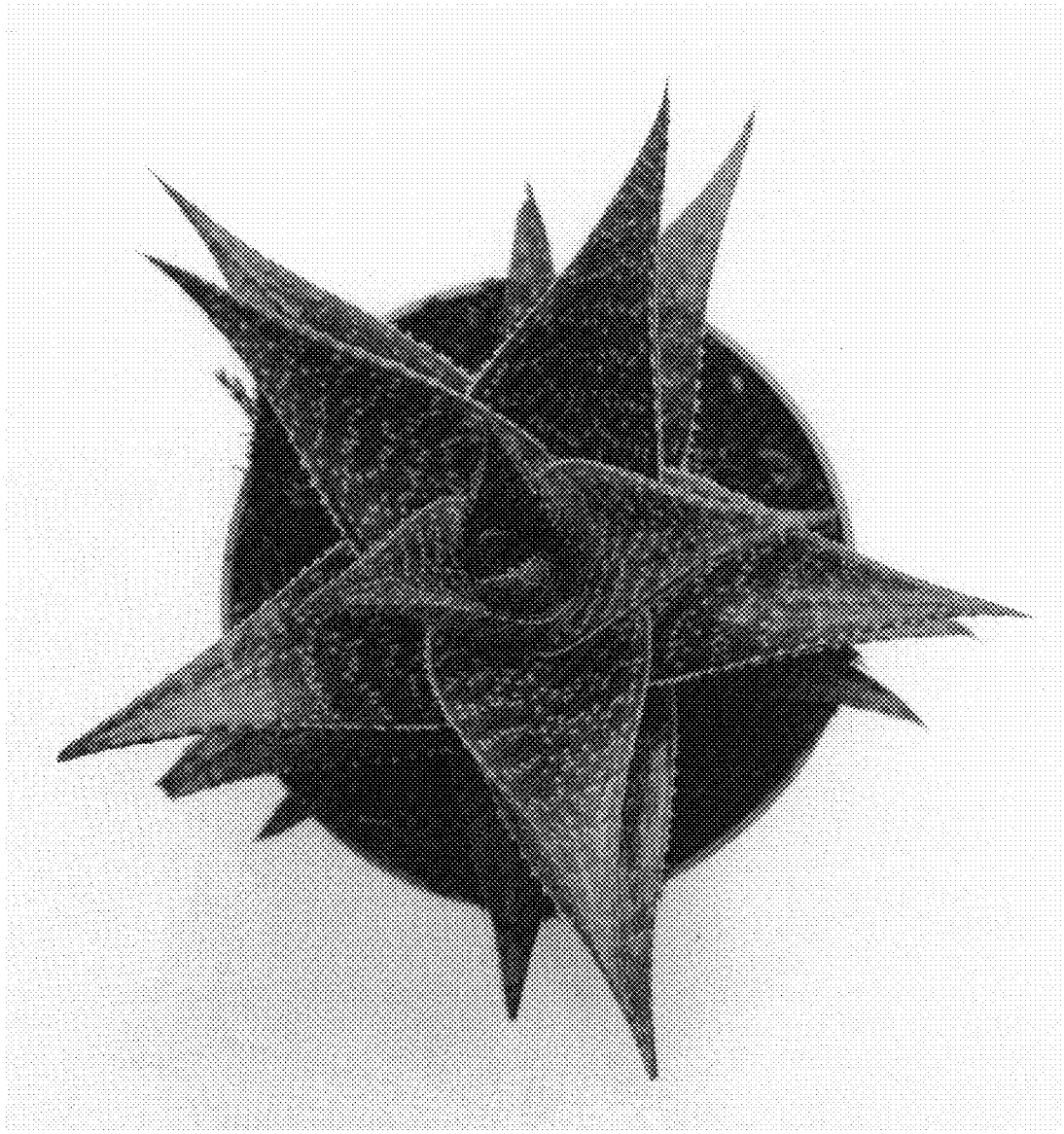
FIG. 2 illustrates, as nearly true as it is reasonably possible to make the same in color photographs of this type, the typical foliage arrangement of 'AMIAL1601.
Figure 3:
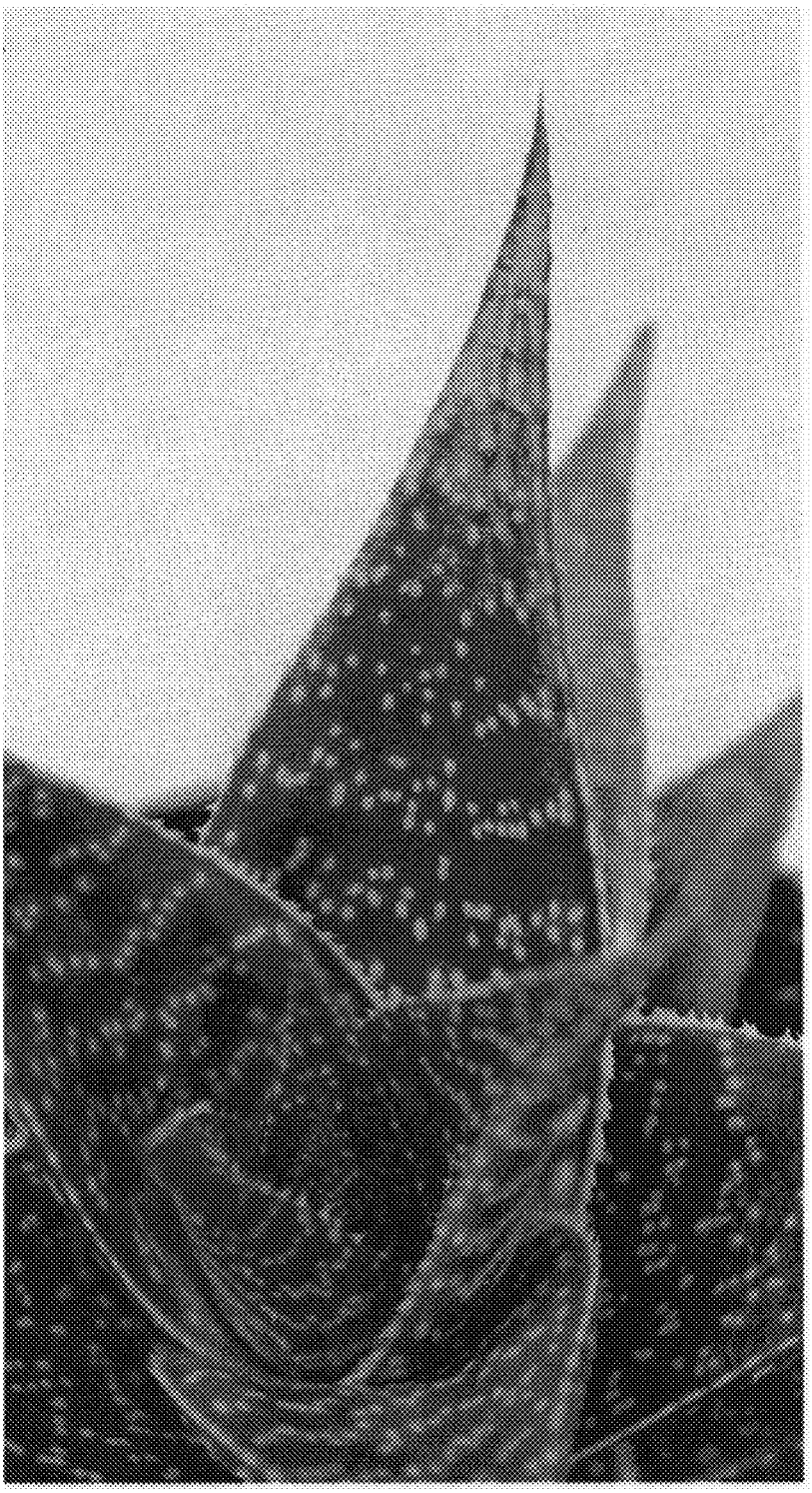
FIG. 3 illustrates, as nearly true as it is reasonably possible to make the same in color photographs of this type, the adaxial surface of the mature foliage 'AMIAL1601'.
Figure 4:
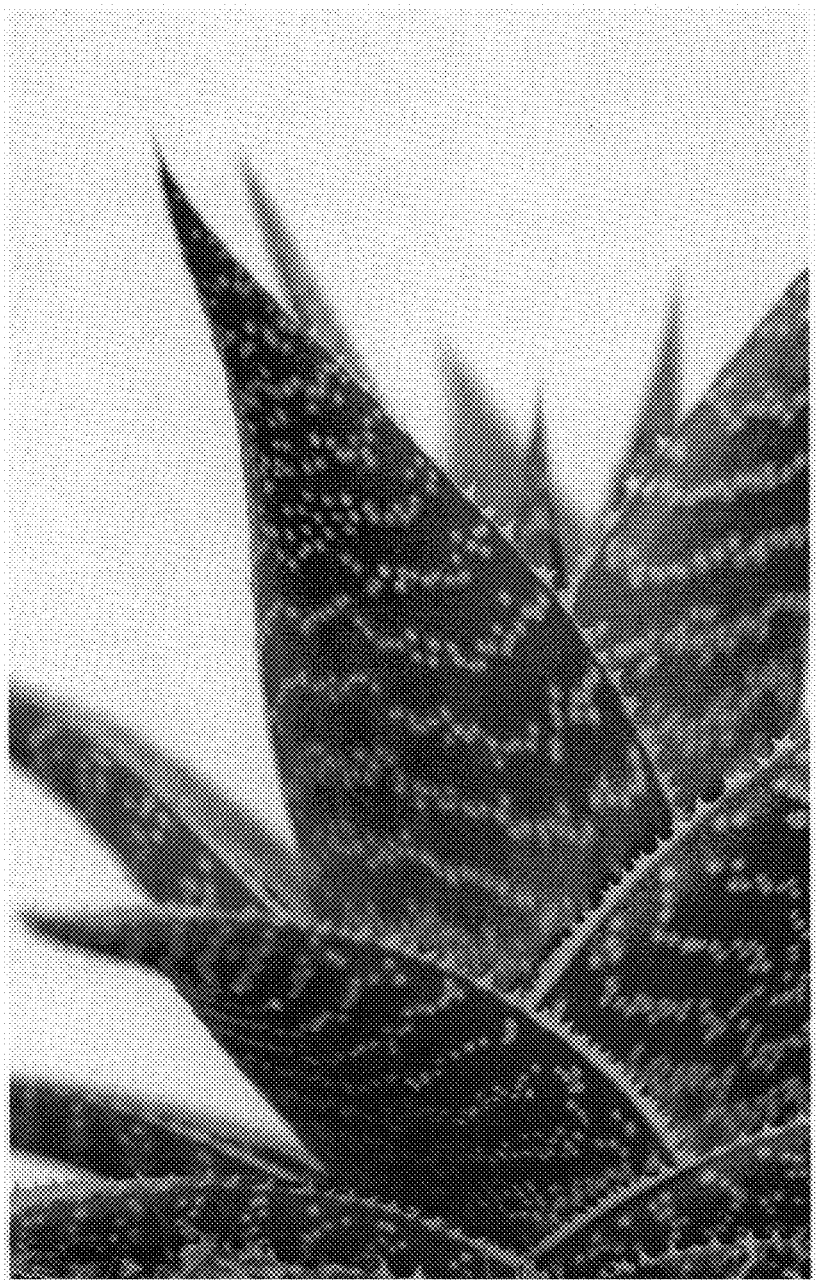
FIG. 4 illustrates, as nearly true as it is reasonably possible to make the same in color photographs of this type, the abaxial surface of the mature foliage 'AMIAL1601'.

The following observations and measurements made in January of 2017 describe averages from a sample set of six specimens of 14 months old 'AMIAL1601' plants grown in 10 cm nursery containers at commercial greenhouse in Heerhugowaard, the Netherlands. Plants were produced using conventional greenhouse production protocols for *Aloe* and *Haworthia* plants which consisted of minimal irrigation and fertilizer applications, and chemical pest and disease control measures against mealy bug, *Botrytis* as required. Plants were grown under approximately 50 percent shade and no photoperiodic treatments or artificial light was given to the plants.

Those skilled in the art will appreciate that certain characteristics will vary with older or, conversely, with younger plants. 'AMIAL1601' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1601' and a comparison with the parents and closest known comparator is provided below.

Plant description:

*Growth habit*.—Succulent perennial with foliage growing in a non-branched basal rosette.

*Plant shape*.—Globular.

*Height from soil level to top of foliar plane*.—10.1 cm.

*Plant spread*.—Average of 15.9 cm.

*Growth rate*.—Low to moderate.

*Plant vigor*.—Moderate.

*Propagation*.—Type — Leaf cuttings and meristematic tissue culture. Time to initiate rooting — Approximately 20 days at 18 degrees Celsius. Crop time — Approximately 30 weeks to produce a marketable plant in a 7 cm container.

*Disease and pest resistance or susceptibility*.—Neither resistance nor susceptibility to typical *Aloe* and *Haworthia* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette comprised of multiple whorls of foliage.

*Division*.—Simple.

*Attachment*.—Sessile.

*Quantity*.—Approximately 5 leaves per whorl and a total of 22 leaves per rosette.

*Shape*.—Thick, succulent leaves; ovate in shape.

*Dimensions*.—9.0 cm long, 3.4 cm wide, and 0.8 cm thick, on average.

*Aspect*.—Slightly concaved and lightly curved downward at an average angle of 40 degrees to horizontal.

*Attitude*.—Inner whorls of foliage are upright; outer whorls of foliage are held more loosely.

*Apex*.—Apiculate, with a soft mucronate tip.

*Base*.—Broad cuneate.

*Margin*.—Finely dentate; teeth have an average length of 0.1 cm and are colored greyed-green, nearest to RHS 192D. Margins are not undulated or lobed.

*Texture, adaxial surface*.—Glabrous and moderately to densely covered with orbicular protuberances arranged in irregular, wavy transverse rows across the leaf surface; protuberances grown into short, soft spines towards the apex, approximately 3.0 mm high and 1.0 mm in diameter.

*Texture, abaxial surface*.—Glabrous and densely covered with orbicular protuberances arranged in irregular, wavy transverse rows across the leaf surface; protuberances grown into short, soft spines towards the apex, approximately 3.0 mm high and 1.0 mm in diameter.

*Luster, adaxial surface*.—Very slightly glossy.

*Luster, abaxial surface*.—Slightly glossy.

*Color*.—Juvenile foliage, adaxial surface — Green, nearest to RHS 143A; fading to yellow-green towards the base, nearest to RHS 146B; darker towards the apex, nearest to a mixture of RHS NN137A and NN137B; protuberances are colored greyed-green, nearest to a mixture of RHS 193C and 193D. Juvenile foliage, abaxial surface — Nearest to a mixture of green and yellow-green, nearest to RHS 143A and 146A; fading to yellow-green towards the base, nearest to RHS N144D; darker towards the apex, nearest to RHS NN137A; protuberances are colored greyed-green, nearest to a mixture of RHS 193C and 193D. Mature foliage, adaxial surface — In between yellow-green, RHS 147A, and greyed-green, RHS N189A; lighter greyed-green towards the base, nearest to RHS 194B; protuberances are colored greyed-green, nearest to a mixture of RHS 191B, 191C, and 191D. Mature foliage, abaxial surface — In between green, RHS 139A, and yellow-green, RHS 147A; fading to a mixture of yellow-green and greyed-green towards the base, nearest to RHS 146A and 194B; protuberances are colored greyed-green, nearest to a mixture of RHS 191B and 191C.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIAL1601' differ from the seed parent, an unnamed *Aloe aristata* (not patented), in the following characteristics described in Table 1 below.

TABLE 1

| Characteristic | 'AMIAL1601' | *Aloe aristata* seed parent |
|---|---|---|
| Plant height. | Taller than the parent. | Shorter than 'AMIAL1601'. |
| Quantity of leaves per whorl of foliage. | Approximately 5 leaves. | Approximately 10 leaves. |
| Leaf size. | Leaves are longer and broader than those of the parent. | Leaves are shorter and narrower than those of 'AMIAL1601'. |
| Leaf thickness. | Leaves are thicker than those of the parent. | Leaves are thinner than those of 'AMIAL1601'. |
| Leaf firmness. | Firmer than those of the parent. | Less firm than those of 'AMIAL1601'. |
| Leaf protuberances. | Protuberances arranged in irregular, wavy transverse rows. | Protuberances are less conspicuous. |

Plants of the new cultivar 'AMIAL1601' differ from the pollen parent, an unnamed *Haworthia limifolia* plant (not patented), in the following characteristics described in Table 2 below.

TABLE 2

| Characteristic | 'AMIAL1601' | *Haworthia limifolia* pollen parent |
|---|---|---|
| Quantity of leaves per whorl of foliage. | Approximately 5 leaves. | Approximately 7 to 15 leaves. |
| Leaf size. | Larger than those of the parent. | Smaller than those of 'AMIAL1601'. |
| Foliage margins. | Finely dentate with larger teeth than those of the parent. | Finely dentate with much smaller teeth than those of 'AMIAL1601'. |
| General coloration of the foliar protuberances. | Very light green. | Green; same color as the leaf surface. |

TABLE 2-continued

| Characteristic | 'AMIAL1601' | *Haworthia limifolia* pollen parent |
|---|---|---|
| Leaf protuberances. | Protuberances arranged in irregular, wavy transverse rows. | Protuberances are less conspicuous. |

COMPARISONS WITH THE CLOSEST KNOWN COMPARATOR

Plants of the new cultivar 'AMIAL1601' differ from the commercial variety, *Gasteria* 'WT03' (Community Plant Variety Rights grant number 30451) in the following characteristics described in Table 3 below.

TABLE 3

| Characteristic | 'AMIAL1601' | 'WT03' |
|---|---|---|
| Foliage attitude. | Inner whorls of foliage are held upright; outer whorls are held more loosely. | Foliage in all whorls is held very upright. |
| Abundance of foliage. | Less abundant. | More abundant. |
| Foliage margins. | Finely dentate with larger teeth than those of 'WT03'. | Finely dentate with smaller teeth than those of 'AMIAL1601'. |
| General coloration of the mature foliage. | Green. | Dark greyed-green. |

That which is claimed is:

1. A new and distinct variety of *Aloe aristata* x *Haworthia limifolia* plant named 'AMIAL1601', substantially as described and illustrated herein.

* * * * *